United States Patent [19]

Degre

[11] Patent Number: 5,085,873

[45] Date of Patent: Feb. 4, 1992

[54] PROCESS FOR THE TREATMENT OF A NON-LIQUID FOOD PRODUCT FOR ASSURING ITS MICROBIAL DECONTAMINATION

[75] Inventor: Michel Degre, Las Tapios

[73] Assignee: Bio Serae Laboratoires S.A., Saint Afrique, France

[21] Appl. No.: 521,978

[22] Filed: May 11, 1990

[51] Int. Cl.$^5$ .......................... A23B 4/20; A23B 4/22; A23L 3/3463

[52] U.S. Cl. .......................................... 426/8; 426/9; 426/10; 426/36; 426/289; 426/310; 426/52; 426/56

[58] Field of Search .................. 426/10, 8, 36, 61, 42, 426/49, 52, 56, 392, 7

[56] References Cited

U.S. PATENT DOCUMENTS

| | | | |
|---|---|---|---|
| Re. 23,523 | 7/1952 | Baker | 426/10 |
| 2,765,233 | 10/1956 | Sarett et al. | 426/10 |
| 4,233,290 | 11/1980 | Ferrari et al. | 426/61 |
| 4,810,508 | 3/1989 | Dell'Acqua et al. | 426/56 |
| 4,867,990 | 9/1989 | Suwa et al. | 426/61 |
| 4,957,749 | 9/1990 | Prieels et al. | 426/61 |

Primary Examiner—Marianne Cintins
Attorney, Agent, or Firm—Harold H. Dutton, Jr.

[57] ABSTRACT

The invention relates to a process for the treatment of a non-liquid food product for assuring its microbial decontamination. This process, applicable to hydrated products containing at least 20% water, comprises depositing on the surface of the hydrated product a preparation called an LP system comprising a mixture of the enzyme lactoperoxidase, a thiocyanate and an oxygen donor. The depositing may in particular be carried out by pulverizing or immersion in a bath. The treatment according to the invention preserves the product against most of the pathogenic or saprophytic germs susceptible of developing on these products, in particular bacteria of the genus Listeria, and in the absence of decomposition of the product and with no risk for the consumer.

18 Claims, No Drawings

PROCESS FOR THE TREATMENT OF A NON-LIQUID FOOD PRODUCT FOR ASSURING ITS MICROBIAL DECONTAMINATION

This invention relates to a process for the treatment of a non-liquid food product, for example cheeses, meats, fish, vegetable products . . . , for assuring their microbial decontamination, in particular vis-a-vis bacteria of the genus Listeria. The invention also relates to preparations permitting the carrying out of said process.

BACKGROUND AND OBJECTS OF THE INVENTION

It is known that food products are frequently the object of microbial contamination, stemming notably from the conditions in which they are actually handled, transported and stored. For example, it has been demonstrated that the generalization of cold storage of these products (at temperatures on the order of 5° C.) reduces the natural development of certain inhibiting agents which resist microbial proliferation. Thus, many food products are carriers of germs at the time of their conditioning, regardless of precautions taken. In particular, bacteria of the genus Listeria have recently produced serious poisonings, particularly from eating contaminated cheeses and meats. Actually, with the exception of drastic thermal treatment, it is not known how to eliminate these bacteria from food products by non-destructive means, compatible with the ultimate consumption of such products. It should be noted in this respect that the conventional operations of seasoning of meats or cheeses preserves the products against most of the serious microorganisms, but has no appreciable effect on the development of certain bacteria, notably bacteria of the genus Listeria (and Yersinia, Campylobacter as well).

The present invention seeks to provide a process for the treatment of non-liquid food products, especially cheeses, meats, processed meats (i.e. pate . . . ), fish, fresh vegetables, etc., in order to decontaminate them in a manner which is quite repressive to the microorganisms susceptible of being developed on these products, in particular bacteria of the genus Listeria, Yersinia, Campylobacter, a group of entero-bacteria, staphylococcus, pseudomonas . . . , in the absence of any destruction of the product and without any risk to the consumer.

Another object is, in the case of cheeses, to provide a decontamination process which preserves the typical flora on the surface of these cheeses, for example the microbial flora which constitute morge (bacterium linens) in the case of morge cheese.

DESCRIPTION OF THE INVENTION

The treatment process according to the invention may be applied to any hydrated food product containing at least 20% water. The process comprises depositing on the surface of the hydrated product a preparation called an LP system, which comprises a mixture of the enzyme lactoperoxidase, a thiocyanate and an oxygen donor. This depositing or coating may be carried out in a liquid form by impregnating the surface of the product with an aqueous phase containing the LP system (pulverizing, immersion in a bath . . . ) or dry by sprinkling over the surface of the product, a powder containing the components of the LP system.

In the case of a food product which is to be processed in contact with a packaging (white cheeses . . . ), the LP system may be deposited on the packaging which serves as a carrier during the conditioning.

Microbiological experiments carried out in a laboratory, as well as tests on samples of food products, have shown that the aforesaid LP system assures a very effective destruction of the Listeria and all other pathogenic organisms usually present in the food products, and for several hours or for several days, depending on the doses applied. This LP system deposited on the surface of the hydrated food product (cheese, meat . . . ) borrows water from the product, initially at the moment of contact (which permits an activation of the system in case of the deposit in the form of a powder), then over time such that the activity of the system is prolonged for rather long periods of time. The enzymatic reaction which is produced on the surface of the solid product is surprising in the current state of enzymological teachings, because it is well known that powerful enzymatic reactions (that is, those benefiting from a very high reaction rate) are only obtained in aqueous liquid media, while enzymatic reactions with solid materials are always very slow and of low efficiency. Thus, it is very unexpected that the LP system which is known per se since it develops naturally in milk (with xanthine oxidase as the oxygen donor) would either be able to decontaminate a solid food product by a simple surface treatment, and in addition, to destroy bacteria as resistant as those of the genus Listeria.

The LP system is strictly non-toxic and very compatible with a food usage since it is found to be contained in certain secretions of mammals (saliva, milk . . . ).

The oxygen donor of the system may be a peroxide, with the preferred proportions of the components then being as follows: between 1 and 4 g of thiocyanate and a quantity of peroxide capable of releasing between 0.4 and 2 g of molecular oxygen, per gram of the lactoperoxidase enzyme.

The oxygen donor may also be the glucose oxidase system, the preferred proportions then being as follows: between 1 and 4 g of thiocyanate and between 0.050 and 0.100 g of glucose oxidase per gram of lactoperoxidase enzyme.

Tests have proven that the effectiveness of the LP system is good when applied in quantities such that the weight of lactoperoxidase enzyme is at least equal to $2.10^{-4}$ mg per $cm^2$ of the surface of the food product. In practice, for limiting costs, the LP system will be deposited such that the quantity of lactoperoxidase will be between $2.10^{-4}$ and $35.10^{-4}$ mg per $cm^2$ of the food product.

In the case of a coating in liquid form, the LP system may even be preliminarily mixed with other agents: a pH salt buffer (citrate, phosphate, acetate, . . . ), or an ionizing salt (NaCl, KCl, . . . ) which permits obtaining an aqueous phase having optimum conditions of stability for the LP system (pH around 5.5, ionizing power corresponding to 10 g of NaCl per l); a foaming agent (sugar ester) for improving the contact of the aqueous phase with the surface of the food product and obtaining a good homogeneity of treatment. A film forming binder (methylcellulose, carboxy-methylcellulose, polyvinyl acetate or propionate . . . ) for better adhering the LP system onto the surface of the food product.

It is also possible to combine with the LP system active components, in particular lactoferrine LF or lysozyme which contribute a complementary antimicrobial activity and produce a synergistic effect with the LP system in the destruction of bacteria, especially bacteria of the genus Listeria as microbiological studies have shown. In addition, one or more fungicidal agents, especially natamycine, sorbic acid and its salts may be added to the system for producing a fungicidal effect.

The invention also relates to particular applications of the process defined above, in particular for decontaminating cheeses with respect to bacteria of the genus Listeria.

Preferably, the LP system to be deposited on the surface of the cheese is placed in solution and/or in suspension in an aqueous phase of a concentration such that the weight of lactoperoxidase per liter of water will comprise between 10 and 500 mg.

In the case of cheese which has been subject to a salting operation during its production prior to aging, the surface treatment by means of the LP system is carried out at least one time during the period of aging.

If the aging period of the cheese is longer than 30 days, preferably a first surface treatment is applied between 10 and 20 days after salting, and at least one other treatment is applied before packaging.

The invention may be applied very favorably for the treatment of cheeses, particularly morge cheeses, comprising a soft paste or a pressed paste, with microbial flora on the surface. Tests have shown that the microbial flora of these cheeses is essentially unaffected by the treatment, such that the characteristics of the cheese are not modified.

The process may be applied to any other hydrated food product for which a problem of contamination, particularly by bacteria of the genus Listeria, may exist, in particular: meats (pieces of meat, carcasses, shredded meat, etc.), pork, fish (fish filets, whole fish), crustaceans and vegetables after harvesting.

The invention also relates to a master preparation intended for the production of the LP system described above preliminarily to the carrying out of the treatment process. This master preparation comprises essentially a mixture of lactoperoxidase enzyme, thiocyanate such as potassium thiocyanate, and an oxygen donor, with if desired, additives: lactoferrine LF, fungicidal compounds, buffer salts, ionizing salts, foaming agents, binding agents, etc.

The lactoperoxidase is actually extracted from milk or from lactoserum by conventional chromatographic processes. The thiocyanate is a compound readily available on the market, and potassium thiocyanate is selected as the preferred compound because of its solubility and its low cost. The oxygen donor may be a peroxide of hydrogen or of magnesium, or a perborate, which compounds are also readily available on the market. It may also be an enzymatic system: glucose-oxidase, which is commercially available and may be used after purification of the enzyme by chromatography.

The master preparation mentioned above is produced in the form of a powder or a concentrated liquid, which is used after dilution either in another pulverulent agent (powder) or in an aqueous phase (concentrated liquid).

Preferably, the oxygen donor of this preliminary preparation is isolated from the other constituents in order to avoid a premature reaction, the constituents not being placed in contact until just before the surface treatment operation. This isolation may be carried out very simply by conditioning the products separately (separate packets for powder, separate compartments in the case of liquid). In the case of powder, it is also possible to separate the oxygen donor by the process described in French patent application 2,600,250, the placing in contact of the components being carried out by hydrosolubilization.

In the case of a liquid preliminary preparation, it may also be placed in solution in an anhydrous polyalcohol, particularly glycerol, which blocks the enzymatic reaction, which is released by placing in aqueous solution.

DESCRIPTION OF DETAILED EMBODIMENTS

The description which follows provides a report of the microbiological studies carried out as well as examples of experimentation in the case of cheeses.

1. Microbioloqical Studies

These studies are intended to verify and quantify the bactericidal activity, in vitro, of two LP systems (LP1, LP2) produced extemporaneously from a lyophilized powder of lactoper-oxidase placed in aqueous solution of various doses with other constituents.

LP1 Composition lactoperoxidase: doses in mg/l, 0.5 or 1 or 5 or 10;
potassium thiocyanate: 25 mg/l;
glucose-oxidase: 1 mg/l.

LP2 Composition lactoperoxidase: doses in mg/l, 5 or 1 or 0.5;
potassium thiocyanate: 25 mg/l
glucose-oxidase: 1 mg/l;
lactoferrine: 50 mg/l.

These systems have been placed in contact with microbial suspensions at $5.10^5$ to $7.10^6$ microorganisms per ml of composition. The incubation lasted 4 hours at a temperature of 37° C., followed by a bacterial count. The table below reports the results obtained with the different strains.

TABLE

| Bacterial Family | LP1 (0.5) | LP1 (1) | LP1 (5) | LP1 (10) | LP2 (0.5) | LP2 (1) | LP2 (5) |
|---|---|---|---|---|---|---|---|
| Listeria | 0 | 0 | ++ | ++++ | 0 | + | +++ |
| Yersinia | 0 | ++ | ++++ | ++++ | 0 | ++ | ++++ |
| Campylobacter | 0 | 0 | ++ | ++++ | 0 | + | +++ |
| 125 Staphylococcus | 0 | + | ++++ | ++++ | 0 | ++ | ++++ |
| Streptococcus | ++ | +++ | ++++ | ++++ | ++ | +++ | ++++ |
| Salmonella | 0 | + | ++++ | ++++ | + | ++ | ++++ |
| E. coli | 0 | + | +++ | ++++ | 0 | ++ | ++++ |
| Pseudomonas | 0 | 0 | ++ | ++++ | 0 | + | +++ |
| Vibrio | 0 | ++ | ++++ | ++++ | + | ++ | ++++ |

For each family of bacteria, several experimental strains (between 2 and 5) were used, from different collections. The results were homogeneous and the average is given in the table. For example, for Listeria, three different strains were tried, from individually produced vegetable ensilage, and two milk products, +signifies a reduction of the number of bacteria by a factor of 10 with respect to the control (existence of an activity of which the intensity remains weak)

++: the same, but a factor of 100 (average activity),

+++: the same, but a factor of 1,000 (good activity),

++++: the same, but a factor of 10,000 (excellent activity).

It has been proven that, at a sufficient dose, the activity is good or excellent for most experimental germs and in particular for the most troublesome germs which are difficult to eradicate by other processes: Listeria, Yersinia, Campylobacter.

2. Treatment of Cheeses

One lot of cheeses of the mold paste type such as munster (hydration of about 55%) was treated according to the process of the invention, while an identical control lot was produced simultaneously under the same conditions without the treatment. These cheeses were prepared by coagulation of standardized, pasteurized milk (75° C., 15 s) with added calcium chloride (0.09M), lactic ferments ($10^6$ cells/ml), Brevibacterium Linens ($10^4$ cells/ml) and animal rennet (0.25 ml/l of milk). The curd is divided, drained and placed in cylindrical molds having a surface area of 300 cm$^2$. After 22 hour of draining, the cheeses are salted with dry salt (2%). Each cheese is then inoculated with Listeria bacteria to simulate a contamination, by means of 1 ml of a suspension of Listeria, the population of which varies between $10^3$ and $10^7$ per ml, with this suspension being arranged uniformly on the surface of each cheese.

Half of the inoculated cheese is treated according to the invention during aging by impregnating each cheese with a homogeneous pulverizate over the entire surface by means of 1 ml of a solution of LP system containing: 20 mg/l of lactoper-oxidase, 25 mg of potassium thiocyanate, and 2 mg of glucose-oxidase.

Samples of the cheeses from the control lots and from the test lots were taken after 4 days of aging at 15° C. (95% humidity) and the population of Listeria was counted on these samples by the FDA method with subculture.

It was determined, after 4 days of aging, that all of the cheeses treated by means of the LP system were completely free of Listeria bacteria, while the control samples had bacteria counts greater than $10^3$ per cm$^2$ of surface. Analyses after 7 days of aging confirmed the complete absence of Listeria on the treated cheeses.

While this invention has been described as having certain preferred features and embodiments, it will be understood that it is capable of still further variation and modification without departing from the spirit of the invention, and this application is intended to cover any and all variations, modifications and adaptations of the invention as fall within the spirit of the invention and the scope of the appended claims.

I claim:

1. A process for the treatment of a non-liquid hydrated food product containing at least 20% of water for assuring the microbial decontamination thereof with respect to bacteria of the genus Listeria, the process comprising depositing on the surface of said hydrated product a quantity of an LP system preparation effective for destruction of pathogenic organisms comprising a mixture of lactoperoxidase enzyme, a thiocyanate and an oxygen donor.

2. A treatment process as in claim 1, comprising depositing the LP system onto the surface of the product by impregnating said surface with an aqueous phase in which the components of the LP system are dissolved and/or dispersed.

3. A treatment process as in claim 2, wherein said impregnation of the surface of the product is achieved by immersing said product in a bath of the aqueous phase containing the LP system.

4. A treatment process as in claims 1, comprising impregnating the surface of the product by pulverizing on said surface the aqueous phase containing the LP system.

5. A treatment process as in claim 1, comprising depositing the LP system onto the surface of the product by sprinkling onto said surface at least one powder containing the components of the LP system.

6. A process as in claim 1, for treating a food product in contact with a packaging, comprising depositing the LP system onto the packaging to contact the surface of the product during packaging.

7. A treatment process as in claim 1, including depositing on the surface of the product an LP system containing between 1 and 4 g of thiocyanate and a quantity of peroxide capable of liberating between 0.4 and 2 g of molecular oxygen per gram of lactoperoxidase.

8. A treatment process as in claim 1, including depositing on the surface of a product an LP system containing between 1 and 4 g of thiocyanate and between 0.050 and 0.100 g of glucose-oxidase as the oxygen donor, per gram of lactoperoxidase enzyme.

9. A treatment process as in claim 7, including depositing the LP system on the surface of the product in a quantity such that the weight of lactoperoxidase enzyme comprises between $2.10^{-4}$ and $35.10^{-4}$ mg per cm$^2$ of surface of the product.

10. A treatment process as in claim 2, including preparing said aqueous phase to be deposited on the surface of the product by adding at least one agent selected from the group consisting of: a pH buffer salt, an ionization salt, a foaming agent, and a film forming binding agent.

11. A treatment process as in claim 1, including adding to the LP system to be deposited on the surface of the product at least one compound selected from the group consisting of lactoferrine, lysozyme, and a fungicidal compound.

12. A treatment process as in claim 1 wherein said food product comprises a cheese for assuring decontamination of said cheese with respect to bacteria of the genus Listeria.

13. A treatment process as in claim 12, including dissolving or suspending in an aqueous phase the LP system to be deposited on the surface of the cheese in a concentration such that the weight of lactoperoxidase per liter of water comprises between 10 and 500 mg.

14. A treatment process as in claim 12 for treating a cheese subjected during the course of its production to a salting operation preceding a period of ageing, and including carrying out the surface treatment by means by means of the LP system at least once during the period of ageing.

15. A treatment process as in claim 14 for treating a cheese during a period of ageing greater than 30 days, and including applying a first surface treatment during a period of between 10 and 20 days after salting, and at least one other treatment before packaging.

16. A treatment process as in claim 15 for treating morge cheese, comprising a mold paste or a pressed mold paste of microbial flora on its surface.

17. A treatment process as in claim 1 comprising treating a food product selected from the group consisting of carcases and pieces of meat, whole and fileted fish and crustaceans.

18. A treatment process as in claim 1 wherein said food product comprises vegetables.

* * * * *